United States Patent [19]
Boigegrain et al.

[11] Patent Number: 5,380,736
[45] Date of Patent: Jan. 10, 1995

[54] HETEROCYCLIC SUBSTITUTED 2-ACYLAMINO-5-THIAZOLES, THEIR PREPARATION AND PHARMACEUTICAL COMPOSITIONS CONTAINING THEM

[75] Inventors: Robert Boigegrain, Assas; Roger Brodin, Montpellier; Danielle Gully, Saubens; Jean-Charles Molimard, Saint Gely du Gesf; Dominique Olliero, Montpellier, all of France

[73] Assignee: Elf Sanofi, Paris, France

[21] Appl. No.: 205,408

[22] Filed: Mar. 3, 1994

Related U.S. Application Data

[62] Division of Ser. No. 889,910, May 29, 1992, Pat. No. 5,314,889.

[30] Foreign Application Priority Data

Jun. 5, 1991 [FR] France ................... 91 06814

[51] Int. Cl.⁶ .......................................... C07D 277/40
[52] U.S. Cl. ...................... 544/369; 546/209; 548/181; 548/184; 548/193; 548/198
[58] Field of Search .............. 548/193, 198, 184, 181; 546/209; 544/369

[56] References Cited
FOREIGN PATENT DOCUMENTS

| | | |
|---|---|---|
| 0208510 | 1/1987 | European Pat. Off. . |
| 0308885 | 12/1988 | European Pat. Off. . |
| 0348523 | 1/1990 | European Pat. Off. . |
| 0432040 | 6/1991 | European Pat. Off. . |
| 3705934 | 9/1988 | Germany . |

OTHER PUBLICATIONS

Bras et al., Chem. Abst., 116-21039y (1991).
Nguyen Minh Thao et al., Chem. Abst., 112-115589x (1989).
Uhlendorf et al., Chem. Abst., 110-231432y (1988).
Nguyen Minh Thao et al., Chem. Abst., 101-171158r (1984).
Bourdais, Chem. Abst., 78-136065t (1972).

Primary Examiner—Robert Gerstl
Attorney, Agent, or Firm—Wegner, Cantor, Mueller & Player

[57] ABSTRACT

Heterocyclic substituted 2-acylamino-5-thiazoles, their preparation and pharmaceutical compositions containing them.

A 2-Acylaminothiazole of formula:

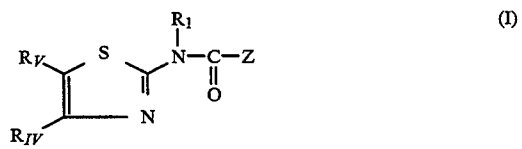

in which $R_1$ is H, an alkyl or a substituted alkyl; $R_{IV}$ is a cycloalkyl, an aromatic group such as phenyl or a heterocyclic group which are unsubstituted or substituted; $R_V$ is a substituted alkyl, a substituted carboxy such as an ester or an amide; or $R_{IV}$ and $R_V$ together represent a phenoxyalkylene group which may be substituted on the phenyl; and Z is a heterocyclic e.g. indolyl group; or a salt of compound (I).

2 Claims, No Drawings

HETEROCYCLIC SUBSTITUTED 2-ACYLAMINO-5-THIAZOLES, THEIR PREPARATION AND PHARMACEUTICAL COMPOSITIONS CONTAINING THEM

This application is a division of Ser. No. 07/889,910, filed May 29, 1992 now U.S. Pat. No. 5,314,889.

The present invention relates to heterocyclic derivatives which interact with the cholecystokinin and gastrin receptor.

Cholecystokinin (CCK) is a polypeptide hormone which occurs in vivo in several forms containing 8 to 39 amino acids. It possesses many physiological activities with respect to the bile ducts, the gastrointestinal tract and on the central and peripheral nervous systems, and reference may be made to the article by J. E. Morley in Life Sciences, 1982, 30, p. 479–493 which presents a detailed review of its properties. Two different populations of CCK receptors have been detected by means of specific antagonists; those of the A type which are present in particular in the pancreas, in the gall bladder and in certain zones of the central nervous system, while those of the B type occur mainly in the central nervous system.

Gastrin is a polypeptide hormone which acts in particular on the acidic secretion of the stomach; its 5 C-terminal amino acids are identical to those of CCK.

Gastrin and/or CCK-antagonising compounds have already been described, in particular proglumide, p-chlorobenzoyl-L-tryptophan, or more recently, substituted benzodiazepines which are specific antagonists either of the CCK A receptors, such as 3S(−)-N-2-[1-methyl-2-oxo-5-phenyl-2,3-dihydro-1H-1,4-benzodiazepin-3-yl]-2-indolecarboxamide (J. Med. Chem., 1988, 31, 2235–46), or of the CCK B receptors, such as 3R(+)-N-[1-methyl-2-oxo-5-phenyl-2,3-dihydro-1H-1,4-benzodiazepin-3-yl]-N'-[3-methylphenyl]urea (Eur. J. Pharmacology, 1989, 162, 273–280).

Thiazole CCK-antagonists are described in P-A-0432 040.

Moreover, substituted thiazoles of formula:

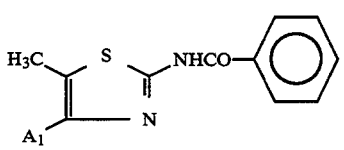

(A)

in which $A_1$ represents a 2,4-dimethoxyphenyl; a 2,3,4-trimethoxyphenyl or a heterocyclic group such as a 3,4-dihydro-7-methoxy-2,2,8-trimethylbenzopyran-1-2H-6-yl or a 3,4-dihydro-7-methoxy-2,2-dimethylbenzopyran-1-yl-2H-6yl are described in Indian J. Chem., Sec. B, 1988, 27 (B) 7, 629–32 as possessing bactericidal or fungicidal properties.

Other substituted thiazoles of formula:

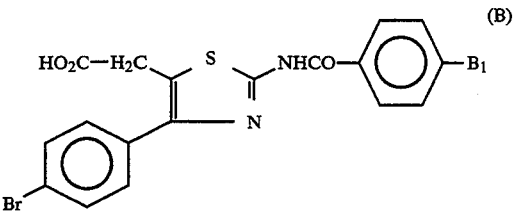

(B)

in which $B_1$ represents hydrogen or a bromine atom are described in Chem. Pharm. Bull., 1977, 25 (9), 2292-9 as possessing anti-inflammatory properties.

Other substituted thiazoles of formula:

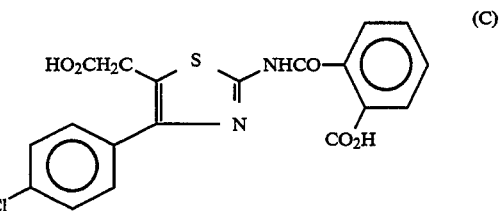

(C)

possess immunostimulant and anti-inflammatory properties and are described in Arch. Immunol. Ther. Exp., 1978, 26 (1–6), 921–9.

Substituted 4-quinolinecarboxamides of formula:

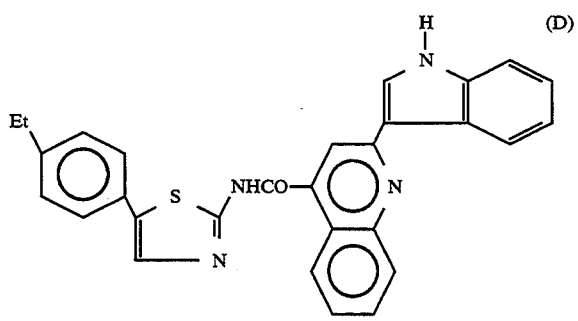

(D)

are mentioned in Chem. Abst. 112 (13), 115 589 x as possessing bactericidal and disinfectant properties.

The compounds according to the invention are heterocyclic substituted 2-aminothiazoles of formula (I):

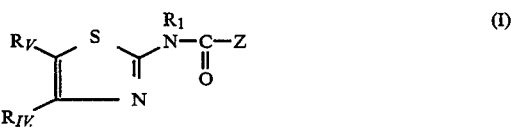

(I)

in which $R_1$ represents a hydrogen atom; a ($C_1$-$C_4$) alkyl group or a phenylalkylene group with a ($C_1$-$C_3$) alkyl; an aminoalkylene group of formula —$Z_1$—$NR_4R_5$ in which $Z_1$ represents a ($C_2$-$C_4$) alkylene and $R_4$ and $R_5$ represent, independently, H or a ($C_1$-$C_4$) alkyl or form with the nitrogen atom to which they are attached, a saturated heterocycle such as morpholino, pyrrolidinyl, piperidino, piperazinyl or ($C_1$-$C_3$) 4-alkylpiperazinyl; an optionally esterified carboxyalkylene group of formula —$Z_2$—$COOR_6$ in which $Z_2$ represents a ($C_1$-$C_4$) alkylene and $R_6$ represents H or a ($C_1$-$C_6$) alkyl; a ($C_2$-$C_5$) cyanoalkylene group; a carbamoylalkylene group of formula —$Z_3$—$CONR_7R_8$ in which $Z_3$ represents a ($C_1$–$C_4$) alkylene and $R_7$ and $R_8$ represent, independently, H or a ($C_1$–$C_4$) alkyl, or with N, a heterocycle such as $NR_4R_5$; a ($C_2$–$C_6$) hydroxyalkylene group, or a ($C_1$–$C_{10}$) alkoxyalkylene group;

$R_{IV}$ represents a ($C_3$–$C_7$) cycloalkyl group which is unsubstituted or substituted by one or more ($C_1$–$C_4$) alkyl groups; an aromatic group such as a phenyl which is unsubstituted or which carries one or more substituents chosen from halogen atoms, in particular chlorine or fluorine, ($C_1$–$C_6$) alkyl, and ($C_1$–$C_3$) alkoxy and thioalkoxy groups, nitro and trifluoromethyl groups or such as a heterocycle containing at least one heteroatom chosen from O, S and N in particular a furyl, thienyl, pyrrolyl, pyrazolyl, imidazolyl, pyridyl, pyrazinyl, oxazolyl and thiazolyl, which are optionally substituted by a ($C_1$–$C_4$) alkyl group or a halogen atom or ($C_1$–$C_4$) alkoxy or $R_{IV}$ and $R_V$, taken together, represent the group:

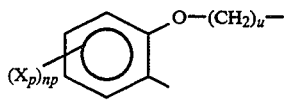

bound through the phenyl carbon in position 4 of the thiazolyl ring and in which u equals 1 to 3, optionally carrying one or more (np) substituents Xp, which are identical or different, chosen from halogen atoms, ($C_1$–$C_3$) alkyl and alkoxy groups, nitro and trifluoromethyl groups, np being equal to 0 to 3;

$R_V$ represents a group —$(CH_2)_m$—X in which m is 0 to 5 and X represents a halogen atom, preferably a bromine atom, a hydroxyl, a ($C_3$–$C_7$) cycloalkyl, a phenyl which may be substituted by one of the groups chosen from halogen atoms, ($C_1$–$C_4$) alkyl or alkoxy groups, or nitro, amino, hydroxyl or trifluoromethyl groups;

a group chosen from —COOH; —$COOX_1$; —O—$COX_1$; —$SCOX_1$; $(O)_q$—S—$X_1$ with q=0.1 or 2;

—O—$COOX_1$; N—CO—$X_1$ with $X_3$ = H or
|
$X_3$ ($C_1$–$C_3$) alkyl; —NH—C—O—$X_1$; —O—C—NH—$X_1$;
          ‖              ‖
          O              O —NH—C—$NHX_1$ with W = O or S;
    ‖
    W —NH—C—$(CH_2)_s$—COOH with s = 2, 3, 4
    ‖
    O in which $X_1$ represents a ($C_1$–$C_5$) alkyl; a phenyl which may be substituted by one or more groups chosen from halogen atoms, ($C_1$–$C_3$) alkyl or alkoxy groups or nitro, amino, hydroxyl or trifluoromethyl groups; an adamantyl group;

a group chosen from —$CONX_1X_2$; —$NX_1X_2$; in which $X_1$ represents hydrogen, a ($C_{13}$–$C_3$) alkyl or a phenyl which is unsubstituted or substituted by one or more groups chosen from halogen atoms, ($C_1$–$C_3$) alkyl or alkoxy groups, or nitro, amino, hydroxyl or trifluoromethyl groups and $X_2$ represents a hydrogen atom, a ($C_1$–$C_3$) alkyl, or alternatively, $X_1$ and $X_2$ constitute, with the nitrogen atom to which they are attached, a heterocycle chosen from pyrrolidine or piperidine which is unsubstituted or substituted by an oxo group or by a hydroxyl group, the latter being unsubstituted or substituted by an acyl, or by a —$COOX_1$ or —$CONX_1X_2$ group;

or alternatively, $R_V$ represents a ($C_1$–$C_5$) alkoxy; a hydroxyl group; a cyclic amine with 5 or 6 members which is unsubstituted or substituted by an oxo group or a hydroxyl group; a piperazinyl group which is unsubstituted or N-substituted by a group —COOAlk in which Alk represents a ($C_1$–$C_5$) alkyl; a carboxylic acid group, a group —$NX_2X_4$ with $X_4$=H or $X_4$=—$(CH_2)_t$—$X_5$, with t equal to 2, 3 or 4 and $X_5$ represents

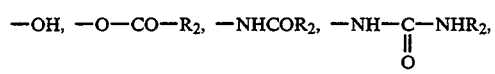

in which $R_2$ represents a ($C_1$–$C_4$) alkyl; or a group —$NR_2R_3$ with $R_2$ or $R_3$ representing independently H, ($C_1$–$C_6$) alkyl, a phenyl group which is unsubstituted or substituted by one or more substituents chosen from halogen atoms or a ($C_1$–$C_3$) alkyl group or a ($C_1$–$C_3$) alkoxy group, or $R_2$ and $R_3$ constitute, with the nitrogen atom to which they are attached, a heterocycle with 5 or 6 members:

Z represents a heterocycle containing one or more heteroatoms chosen from O, S and N, coupled to an aromatic nucleus which may also contain a heteroatom chosen from O, S and N and which may be substituted by one or more groups chosen from halogen atoms, ($C_1$–$C_3$) alkyl and alkoxy groups, or benzyloxy, nitro, amino and trifluoromethyl groups, it being possible for the heteroatom N to be aromatic or in the form of —NH which is unsubstituted or substituted by ($C_1$–$C_4$) alkyl, carboxyalkylene —$Z_4$—$COOR_{10}$ in which $Z_4$ represents ($C_1$–$C_4$) alkylene and $R_{10}$ is H, benzyl or ($C_1$–$C_6$) alkyl; carbamoylalkylene —$Z_5$—$CONR_{11}R_{12}$ in which $Z_5$ represents ($C_1$–$C_4$) alkylene and $R_{11}$ and $R_{12}$ represent, independently, H, ($C_1$–$C_4$) alkyl, or form with N a saturated heterocycle such as morpholino or piperidino; acyl $COR_{13}$ with $R_{13}$ representing ($C_1$–$C_4$) alkyl or phenyl; alkoxycarbonyl —$COOR_{14}$ with $R_{14}$ being tert-butyl or benzyl;

as well as the addition salts of these compounds with inorganic or organic acids and bases; the pharmaceutically acceptable nontoxic salts are prepared but other salts which may be used to isolate or purify the compounds of formula (I) are also within the invention.

The alkyl, alkylene, alkoxy and thioalkoxy groups may be linear or branched.

Z represents in particular benzothienyl, benzofuranyl, benzoxazolyl, benzimidazolyl, benzothiazolyl, indolyl, isoindolyl, indolinyl, isoindolinyl, quinolyl, isoquinolyl, quinoxalinyl, quinazolinyl, cinnolinyl and [2,3-c]-thieno or [3,2-c]-pyridyl.

When Z represents an indolyl group of formula:

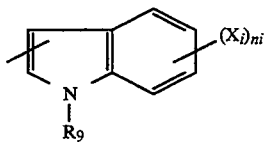

in which $(X_i)_{ni}$ represents the optional substituents of the aromatic nucleus, $R_9$ may represent H; a $(C_1-C_4)$ alkyl group; an optionally esterified carboxyalkylene group of formula $-Z_4-COOR_{10}$ in which $Z_4$ represents a $(C_1-C_4)$ alkylene and $R_{10}$ represents H, a benzyl or a $(C_1-C_6)$ alkyl; a carbamoylalkylene group of formula $-Z_5-CONR_{11}R_{12}$ in which $R_{11}$ and $R_{12}$ represent, independently, H or a ($C_1-C_6$) alkyl or form with N a saturated heterocycle chosen from morpholino or piperidino and $Z_5$ is a $(C_1-C_4)$ alkylene; an acyl group of formula $COR_{13}$ in which $R_{13}$ represents a $(C_1-C_4)$ alkyl or a phenyl; an alkoxycarbonyl group of formula $COOR_{14}$ in which $R_{14}$ represents tert-butyl or benzyl.

Among the compounds of formula (I), those in which $R_1$ represents hydrogen are preferred and among these, more particularly those in which Z represents an indolyl group which is substituted or unsubstituted on the nitrogen; among the groups $R_{IV}$, phenyl is preferred.

The subject of the present invention is also the preparation of the compounds of formula (I) which are prepared by a coupling reaction of an aminothiazole of formula (II):

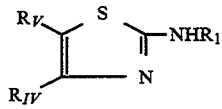 (II)

in which $R_1$, $R_{IV}$ and $R_V$ have the meanings given for (I), under the usual conditions for the acylation of an amine group, with an acid of formula Z'COOH in which Z' represents Z or a substituted Z in which the reactive groups of Z have been protected, and $R_1$, $R_V$, $R_{IV}$ and Z have the same meaning as in the formula (I), or with an activated form of the acid Z'COOH, such as an acid halide, an acid anhydride, and preferably a mixed anhydride such as a carbonic anhydride, or an activated ester, obtained with the reagents commonly used in peptide synthesis.

The compounds (II) may be protected; in this case, $R_1^o$ represents the same substituents as $R_1$ in which the amino group which is present is N-protected, $R_{IVa}$ and $R_{Va}$ represent the same substituents as $R_{IV}$ and $R_V$ in which the hydroxyl or amino groups are O- and N-protected.

Once the groups have been protected, the appropriate deprotection reaction is carried out, if necessary, after the condensation.

Numerous aminothiazoles of formula (II) are known.

The new aminothiazoles may be prepared according to one of the methods described in particular in Bull. Soc. Chim. (C) 1963, 2498–2503.

Generally, a thiourea will be reacted with an alpha-halogenated, and preferably alpha-brominated ketone, according to the following reaction scheme:

SCHEME 1

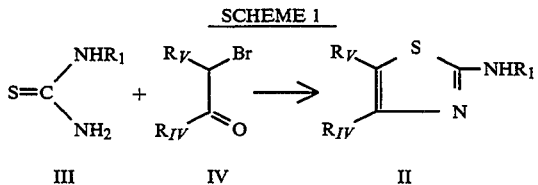

$R_1$, $R_{IV}$ and $R_V$ having the same meaning as in the formula (II).

The preparation of various compounds (II) in which $R_1$ represents an aminoalkyl group is described in EP-A-0,283,390.

The alpha-halogenated ketones and the thioureas may be prepared by methods the principles of which are described in the literature; thus, the alpha-brominated ketones (IV) may be prepared by reacting $R_VCH_2COR_{IV}$ with bromine in acetic acid medium or with cuptic bromide in an organic solvent such as ethyl acetate, a chlorine-containing solvent or mixtures thereof. The starting aromatic ketones are generally prepared by Friedel-Crafts reaction, whereas the aliphatic methyl ketones may be prepared by reacting diazomethane with appropriate carboxylic acid chlorides followed by hydrolysis of the corresponding diazoketone.

The alpha-chlorinated aromatic ketones may be prepared by Friedel-Crafts reaction with the appropriate alpha-chlorinated acid chloride.

When $R_V$ represents an ester group $(CH_2)_m-COOX_1$, the corresponding substituted thiazoles of formula (V) below in which $R_{IV}$, $X_1$ and m are as defined for (I) are known or are prepared according to known methods by reacting an alpha-bromoaceto acid or an alpha-bromoketo ester with the thiourea according to the following reaction scheme:

SCHEME 2

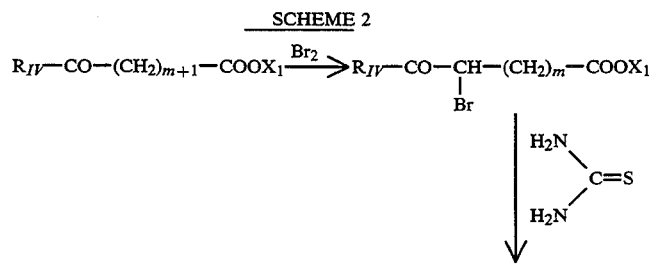

SCHEME 2

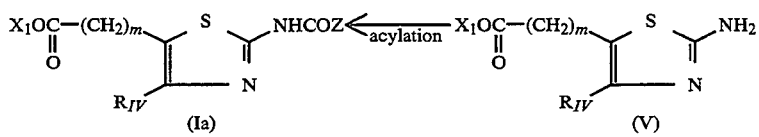

Depending on the value of the substituent $R_V$, the following methods of preparation are used:

a) when $R_V$ represents a group —$(CH_2)_m$—OH, the corresponding substituted 2-aminothiazole of formula (VI) below, in which m is as defined for (I), may be prepared from the above esters (V) by reduction with an alkali metal hydride such as for example lithium aluminium hydride in an aprotic solvent such as for example tetrahydrofuran to give the aminoalcohol of formula:

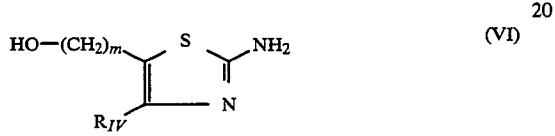

the acylation of (VI) with ZCOOH leads to the compound (Ib) of formula:

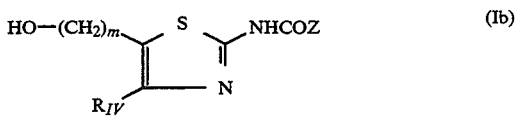

in which formulae m, $R_{IV}$ and Z are as defined for (I);

b) when $R_V$ represents an ester group —$(CH_2)_m$—O—CO—$X_1$ or a thioester group —$(CH_2)_m$—S—$COX_1$ or $(O)_q$—S—$X_1$, in which m, $X_1$ and q are as defined for (I), the substituted 2-aminothiazoles (VII), (VIIc) or (VIId) in which the groups $R_{IV}$, q, m, W and $X_1$ are as defined for (I), may be prepared either according to the following Scheme 3:

SCHEME 3

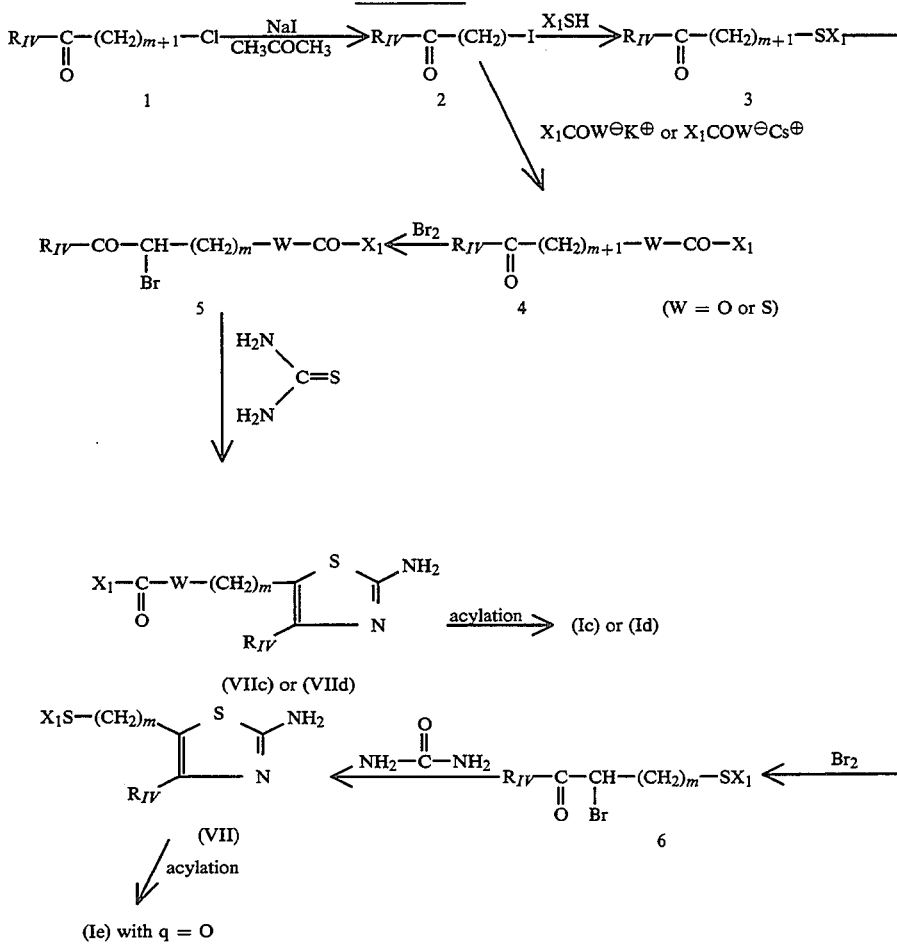

or from N-protected alcohols (VI) such as defined above which are reacted with an acid chloride such as for example acetyl chloride in a solvent such as for example pyridine, to obtain the esters of formula:

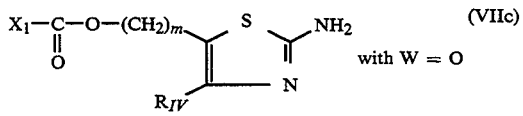

or

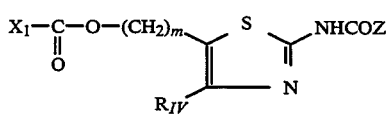

in which $X_1$, m, $R_{IV}$ or Z are as defined above for (I);

c) when $R_V$ represents a carbamate —$(CH_2)_m$—O—CO—NHX$_1$ in which m and $X_1$ are as defined for (I), the substituted thiazoles according to the invention are prepared from the corresponding hydroxylated compounds (Ib), by reacting an isocyanate of formula $X_1$—N=C=O, in an aprotic solvent such as for example tetrahydrofuran or dichloromethane at a temperature of between 20° C. and 100° C., to give the compound (If) of formula:

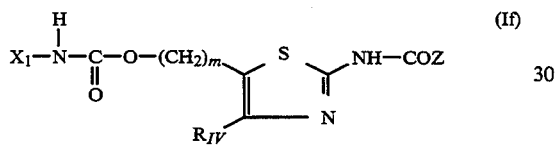

in which $X_1$, m, $R_{IV}$ and Z are as defined for (I);

d) when $R_V$ represents an amide —$(CH_2)_m$—CONX$_1$X$_2$ in which m, $X_1$ and $X_2$ are as defined for (I), the thiazoles according to the invention are prepared by reacting the amine NHX$_1$X$_2$ with the corresponding ester of formula (V) or (Ia) in the presence or in the absence of a solvent such as an alkanol, at a temperature of between 20 and 120° C.; the reaction may also be carried out in a sealed tube depending on whether the amine is volatile, to give the compound (VIII) or (Ig) of formula:

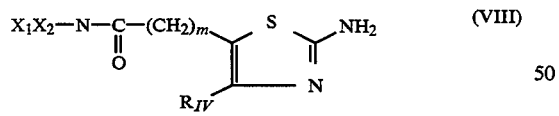

or

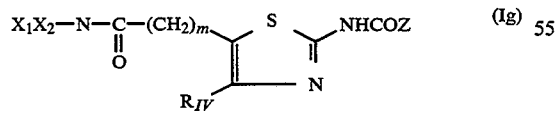

in which $X_1$, $X_2$, m, $R_{IV}$ and, optionally, Z are as defined for (I);

e) when $R_V$ represents an amine group —$(CH_2)_m$—NX$_1$X$_2$, the substituted thiazoles according to the invention are prepared, for example, by reduction of the abovedescribed amides of formula (VIII) by reduction with an alkali metal hydride such as for example lithium aluminium hydride in a solvent such as tetrahydrofuran, at a temperature of between 20° C. and the boiling temperature of the solvent, to give the compound of formula:

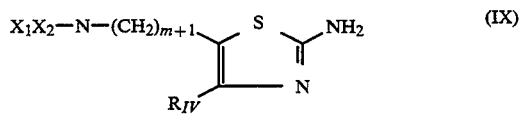

the acylation of (IX) with ZCOOH gives the compound (Ih) of formula:

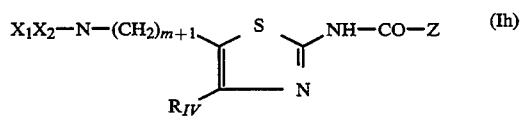

in which $X_1$, $X_2$, m, $R_{IV}$ and Z are as defined for (I);

f) when $R_V$ represents a carbonate —$(CH_2)_m$—O—COOX$_1$, in which m and $X_1$ are as defined for (I), the thiazoles according to the invention are prepared from the alcohols (Ib) by reacting them with a chloroformate

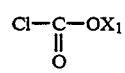

in the presence of a base such as triethylamine or pyridine, to give the compound (Ii) of formula:

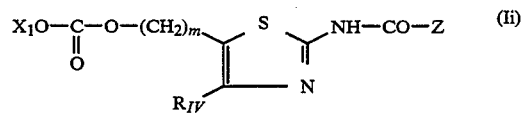

in which $X_1$, m, $R_{IV}$ and Z are as defined for (I);

g) when $R_{IV}$ and $R_V$ taken together represent the group:

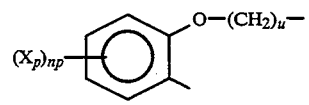

in which $(X_p)_{np}$ and u are as defined for (I), bound via the phenyl carbon in position 4 of the thiazole nucleus; for example, the intermediate 4-bromo-2H-dihydro-3,4-[1]-benzoxepin-5-one of formula:

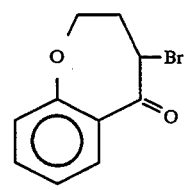

is prepared according to G. Fontaine et al., C. R. Acad. Sci., 1965, 258, 4583; the 2-amino-4,5-dihydro-[5,4-d]-thiazolo-[1]-benzoxepine of formula:

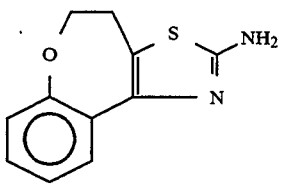
(X)

is prepared by cyclisation with the thiourea according to the usual method described above, and then acylated to give the compound of formula:

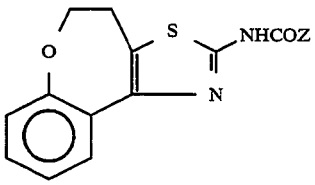
(Ij)

in which Z is as defined for (I);

h) when $R_V$ represents an amino group $-NX_2X_4$, in which $X_2$ and $X_4$ are as defined for (I), the substituted thiazole according to the invention may be prepared from the 2-amino-5-bromothiazole of formula:

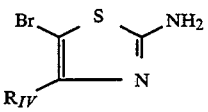
(XI)

which is prepared according to J. Chem. Soc., 1947, 114, which is then:

either acylated, for example, with a substituted ZCOOH, in the presence of BOP and a base such as triethylamine, and then this brominated derivative obtained of formula:

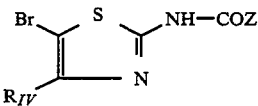
(Ik)

in which $R_{IV}$ and Z are as defined for (I), is substituted by an amine $HNX_2X_4$ in an alkanol at a temperature of between 20° C. and the boiling temperature of the solvent, to give the compound of formula:

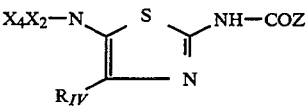
(Il)

in which $X_2$, $X_1$, $R_{IV}$ and Z are as defined for (I), or substituted by the amine $HNX_2X_4$ and then acylated in position 2 of the thiazole, the two reactions being carried out under identical conditions to those described above;

i) when $R_V$ represents a group $-(CH_2)_m-X$, in which m=0 and X represents a $(C_1-C_5)$ alkoxy group the corresponding 2-aminothiazole is prepared from 2-bromo-2-alkoxy-1-phenylethanone, which is optionally substituted on the phenyl, to give the product of formula:

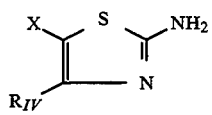
(XI')

in which $R_{IV}$ is as defined above and X represents a $(C_1-C_5)$ alkoxy, which is then acylated as indicated above to give the compounds (Im) of formula:

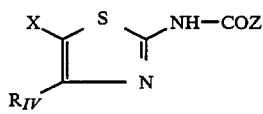
(Im)

in which $R_{IV}$ and Z are as defined for (I) and X is as defined above for (XI'), or one of their salts.

The compounds of formula (XI') are new intermediates which are also within the invention.

Some of the acids ZCOOH or Z'COOH, are known and are even available commercially; the others are prepared using the methods known for similar molecules.

Thus, the indolecarboxylic acids, hereafter called Z"COOH; of formula:

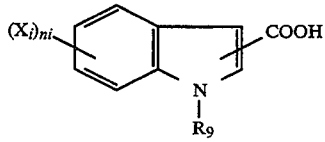

in which $R_9$ represents an alkoxycarbonylalkylene group may be prepared from indolecarboxylic acids, which are commercially available or which are obtained by conventional methods, using the reaction scheme 4 below.

SCHEME 4

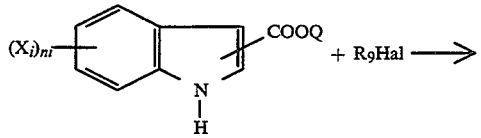

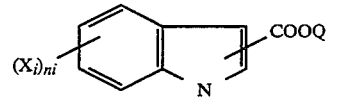

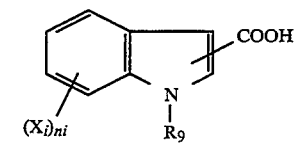

in which Hal represents a halogen atom and Q represents a benzyl group.

The benzyl esters of scheme (4) are prepared by reacting the corresponding acid with benzyl alcohol, in the presence of one of the acid group-activating agents which are commonly used in peptide synthesis, such as:

1,1'-carbonyldiimidazole for which reference can be made to Synthesis 1982, p. 833, N,N-dicyclohexylcarbodiimide, in the presence of 4-dimethylaminopyridine, for which reference can be made to J. Org. Chem. 1990, 55 (4), p. 1390, benzotriazolyloxytris(dimethylamino)phosphonium hexafluorophosphate for which reference can be made to Synthesis, 1977, p. 413.

The base used during the binding of $R_9$ to the nitrogen of the benzyl ester is preferably an anhydrous strong base such as an alkali metal hydride; the reaction mixture is in this case an aprotic polar solvent, which is stable in the presence of a strong base such as dimethylformamide or dimethoxyethane; the reaction is carried out at a temperature of between about 15° C. and 80° C.

The removal of the benzyl group after the N-alkylation, is carried out in a conventional manner by reacting not less than one equivalent of hydrogen, in the presence of a catalyst such as palladium on carbon, with the ester dissolved in an alcohol or dimethylformamide, optionally under a mild pressure.

Moreover, some ZCOOH acids are not very stable or carry a group which may react during the coupling with aminothiazole and it is preferable to use them in a protected form Z'COOH.

Thus, the derivatives (I) in which Z represents:

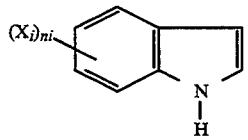

and in which $(X_i)_{ni}$ represents the optional substituents, may be prepared from the compounds obtained by coupling the aminothiazole to compounds of the indolecarboxylic acid Z'COOH, of formula:

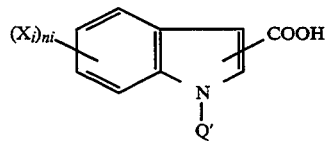

(XII)

in which Q' represents a group which is normally used for the protection of $NH_2$ groups in amino acid coupling reactions, such as

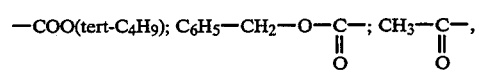

the protective group Q may be removed from the compound of formula:

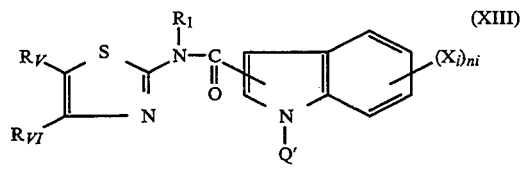

(XIII)

which is obtained after coupling to the derivative (II), by conventional deprotection methods.

BOC may be removed by pyrolysis, in the absence of solvent, at a temperature of between 180° and 200° C.

The indolecarboxylic acids Z"COOH in which $R_9$ is $COOC(CH_3)_3$ or $COOCH_2C_6H_5$, may be prepared by reacting tert-butyl dicarbonate or benzyl chloroformate with Z"COOH in which $R_9=H$, in the presence of a base such as triethylamine or 4-dimethylaminopyridine, in a solvent such as acetonitrile or methylene chloride.

The acids Z"COOH in which $R_9$ is an acyl group, may be prepared by reacting the acid chloride or anhydride with Z"COOH, in which $R_9=H$, in the presence of one equivalent of triethylamine and 4-dimethylaminopyridine, for example in dichloromethane.

The acid chloride of formula ZCOCl, may be prepared, in particular by reacting $SOCl_2$ or a mixture of $POCl_3$ and $P_2O_5$ with the corresponding acid, in general in the absence of solvent and at the reflux temperature of the reaction mixture.

Among the activated esters of formula ZCOOY", Z'COOY" or Z"COOY", those in which Y" represents

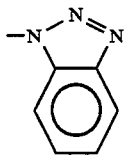

may be prepared by reacting 1-hydroxybenzothiazole with the acid in the presence of dicyclohexylcarbodiimide according to the procedure described in J. Am. Chem. Soc. 1971, 93, 6318–6319 (1971), or by reacting 1-benzothiazolyloxytris(dimethylamino)phosphonium hexafluorophosphate according to the procedure described in Synthesis, 1976, 751–752.

The coupling of the aminothiazole (II) with the acid in activated ester form, may be carried out in a solvent the nature of which is chosen according to the solubility of the compounds and the type of activation of the acid group, preferably in the presence of a base, for example a tertiary amine such as triethylamine; the reaction is generally carried out at a temperature of between 0° C. and 30° C.

When the compounds of formula (I) contain a carboxylic acid group in Z, they are prepared by hydrolysis of an ester preferably in a base medium, for example by reaction of an inorganic base such as an alkali metal hydroxyl, in a dilute alcoholic medium or by acid hydrolysis in the case of a tert-butyl ester.

The addition salts of the compounds of formula (I) with acids or bases are prepared in the usual manner by introducing the acid or the base into a solution of the compound of formula (I). The salt is isolated, depending on its solubility properties, after evaporation of the solvent or addition of a non-solvent.

The compounds of formula (I) and their salts inhibit the binding of cholecystokinin to its receptors. They are more or less selective for the A or B type receptors, and for more or less potent gastrin antagonists.

Their affinity for the CCK A receptor has been determined in vitro using the method described below, the principle of which is that mentioned in Life Sciences, 1985, 37, (26), 2483-2490; it consists in determining the displacement of iodinated CCK 8S from its receptors, in a rat pancreas homogenate: aliquot amounts of pancreatic membrane suspension (100 μg of proteins per ml) in a TRIS-HCl buffer (50 mM), of pH=7.4, containing $MgCl_2$ (5 mM), bacitracin (0.1 mg/ml), methylphenylmethanesulphonic acid fluoride (0.1 mg/ml), are incubated for 40 minutes at 25° C. in the presence of iodinated CCK 8S (2000 Ci/mmol, equivalent to 50 mM final concentration) and of increasing concentrations of the test substance; the reaction is stopped by centrifugation after 40 minutes. After removal of the supernatant, the radioactivity of the pellet is measured. Moreover, nonspecific binding is determined in the presence of CCK 8S at a concentration of 1 μM.

Under these conditions, the concentration inhibiting binding by 50% ($IC_{50}$) is less than $10^{-7}M$ for the products of the invention, and, for many, is about $10^{-10}M$.

Their affinity for the CCK B receptors was determined by studying the displacement of iodinated CCK 8S from its specific receptors which are present in guinea pig cortex homogenates, using the same procedure as for the CCK A receptors, but for a membrane suspension containing 600 μg of proteins/ml with a HEPES buffer (10 mM) at pH 6.5, containing NaCl (130 mM), $MgCl_2$ (5 mM), EDTA (1 mM) and bacitracin (250 mg/ml) and the incubation being for 2 hours.

At a concentration of $10^{-5}M$, all the products displace more than 25% of the labelled CCK 8S from the B receptor; some have a $IC_{50}$ of about $10^{-9}M$.

The affinity for the gastrin receptor of the most CCK B receptor-specific compounds was studied according to the method described below, the principle of which is that mentioned in J. Receptor. Res., 1983, 3 (5) 647-655; aliquots of guinea pig gastric glands in a HEPES buffer, pH=7.4 (24.5 mM), containing NaCl (98 mM), KCl (6 mM), $NaH_2PO_4$(2.5 mM), pyruvate (5 mM), $CaCl_2$ (0.5 mM), $MgCl_2$ (1 mM), glucose (11.5 mM), glutamine (1 mM), bovine albumin (0.4 g/100 ml) were incubated for 90 minutes at 37° C. in a water bath in the presence of iodinated gastrin (2-17) (2000 Ci/mmol; 70 pM) and of increasing concentrations of the test products. The reaction was stopped by centrifugation and the radioactivity of the pellet measured; the nonspecific binding was determined in the presence of gastrin (2-17) at 1 μM. The compounds of the invention have a $IC_{50}$ of between $10^{-5}M$ and $10^{-9}M$.

It has also been shown that the compounds of the invention have an inhibitory activity with respect to that of CCK. This has been demonstrated in vitro by measuring the inhibition by the test products, of CCK 8S-stimulated secretion of amylase by rat acinar cells, according to a method similar to that described in J. Biol. Chem., 1979, 254 (12), 5321-5327, but with guinea pig pancreatic tissues. The compounds have a $IC_{50}$ of $10^{-6}M$ to $10^{-9}M$.

Finally, in vivo, in mice, the compounds having a good affinity for the CCK A receptors antagonised the inhibition of the emptying of the stomach induced by subcutaneous administration of CCK 8S in the procedure described in Life Sciences, 1986, 39, 1631-1638; the $ED_{50}$ (effective dose 50) thus determined is substantially lower than that of proglumide, a known gastrin antagonist.

As these compounds are not very toxic, they can be used as medicines for the treatment of physiological disorders resulting from a hypersecretion of these peptides or from a dysregulation of the biological hormonal systems in which they are involved, in the region of the intestinal sphere or in the central nervous system, depending on their specificity. Reference can be made to the review of the therapeutic applications of the antagonists of CCK and gastrin, published in "Proceedings of International Symposium on Gastrin and Cholecystokinin" 7-11 Sept. 1987—Ed. J. P. Bali, J. Martinez —Elsevier Science Pub. BV.

In particular, the antagonists of CCK will be useful in the treatment of intestinal dyskinesias such as irritable colon syndrome, in the treatment of acute or chronic pancreatitis or in that of pancreatic carcinomas, but also for regulating appetite, or, combined with opium-containing analgesics, in the treatment of pain.

As for the more selective gastrin antagonists, they will be useful in the treatment and prevention of gastric ulcers, in the treatment of Zollinger-Ellison syndrome, in that of hyperplasia of the G cells of the antrum or for patients with cancerous tumours of the oesophagus, of the stomach or of the intestine.

Among the antagonists of cholecystokinin at the level of the A receptors, the following compounds are preferred:

2-[(1-Carboxymethyl-2-indolyl)carbonylamino]-4-phenyl-5-acetoxyethylthiazole.

2-[(2-Indolyl)carbonylamino]-4-phenyl-5-acetoxyethylthiazole.

The medicines according to the invention contain at least one of the compounds of the formula (I) or one of its salts with a pharmaceutically acceptable acid or base, optionally combined with the usual excipients so as to constitute a pharmaceutical composition which can be administered in a conventional manner via the oral, transmucous, parenteral or rectal route. The doses administered depend on the nature and the severity of the disease, on the compound and on the route of administration. They will be generally between 20 and 100 mg per day in an adult man via the oral route and 3 to 10 mg by injection.

The pharmaceutical compositions according to the invention can be, for oral administration, provided in the form of tablets, pills, hard gelatin capsules or granules or alternatively in the form of a solution,. suspension or gel. For parenteral administration, the compositions of the invention will be provided in the form of a solution, suspension or emulsion in an oil or any solvent for injection, optionally aqueous based containing conventional adjuvants for this type of formulation.

For local administration, on the skin or on the mucous membranes, the compositions according to the invention will be provided as a cream, ointment or in the form of a transdermal device, whereas for rectal administration, they will be in the form of suppositories and rectal capsules.

In the following text, examples of implementation of the invention are described as well as methods of preparing certain synthesis intermediates of formula II and IV. The melting points, m.p., indicated were determined in capillary tubes. The nuclear magnetic resonance (NMR) spectra were recorded relative to tetramethylsilane.

PREPARATION A

2-Aminothiazole substituted in position 5 by a group —(CH$_2$)$_m$X$_1$

2-Amino-4-(2,4-dimethoxyphenyl)-5-benzylthiazole

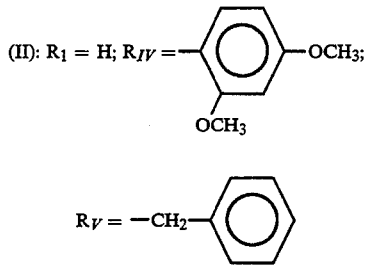

(II): R$_1$ = H; R$_{IV}$ = [2,4-dimethoxyphenyl];

R$_V$ = —CH$_2$—[phenyl]

A) 1-(2,4-Dimethoxyphenyl)-3-phenylpropan-1-one is prepared according to E. Thomas et al., J. Med. Chem., 1985, 28, 442–446 via the Friedel-Crafts reaction.

B) 1-(2,4-Dimethoxyphenyl)-2-bromo-3-phenylpropan-1-one is prepared according to conventional methods by bromination using bromine in a solvent such as dichloromethane or carbontetrachloride.

C) 2-Amino-4-(2,4-dimethoxyphenyl)-5-benzylthiazole.

4.35 g of thiourea are added to 10 g of the brominated derivative prepared above, dissolved in 100 ml of 95° ethanol and the reaction mixture is refluxed for three hours. The mixture is concentrated under vacuum and the residue is taken up in dichloromethane and then washed with a saturated solution of Na$_2$CO$_3$. The organic phase is separated by decantation, dried over MgSO$_4$ and concentrated under vacuum. The residue crystallises from 50 ml of dichloromethane.

m = 7.10 g; m.p. = 202°–203° C.

By carrying out the procedure as indicated above, the 2-aminothiazoles described in Table 1 below are prepared.

TABLE 1

[Structure: X—(CH$_2$)$_m$ attached to C=C with S-C(NH$_2$)=N thiazole ring, and phenyl with r$_4$ and r'$_4$ substituents]

| X—(CH$_2$)$_m$— | r$_4$ | r'$_4$ | m.p; °C. |
|---|---|---|---|
| cyclohexyl-CH$_2$— | —OCH$_3$ | —OCH$_3$ | 119 |
| phenyl- | —OCH$_3$ | —OCH$_3$ | 163–164 |
| 2-methoxyphenyl- | —OCH$_3$ | —OCH$_3$ | 162 |
| 3-methoxyphenyl- | —OCH$_3$ | —OCH$_3$ | 121 |
| 4-methoxyphenyl- | —OCH$_3$ | —OCH$_3$ | 176 |

PREPARATION B

2-Aminothiazole substituted in position 5 by a group —(CH$_2$)—CO$_2$X$_1$ or —(CH$_2$)$_m$—CH$_2$OH A) 2-Amino-4-phenyl-5-methoxycarbonylmethylthiazole.

(II): R$_1$=H; R$_{IV}$=—C$_6$H$_5$; R$_V$=—CH$_2$—CO$_2$CH$_3$

Prepared according to E. Knott, J. Chem. Soc., 1945, 455.

B) 2-Amino-4-phenyl-5-hydroxyethylthiazole.

5 g of the amino ester prepared above is added to a suspension of 2 g of lithium aluminium hydride in 100 ml of tetrahydrofuran cooled to 0° C., and the reaction mixture is refluxed for two hours. 2 ml of water, 1 ml of concentrated NaOH and 6 ml of water are then added successively after cooling on an ice bath and then the reaction mixture is stirred overnight. The inorganic matter is separated by filtration and the mother liquors are concentrated under vacuum. The residue is taken up in dichloromethane, washed with water and the organic phase is successively decanted, dried over MgSO$_4$ and concentrated under vacuum. The residue is chromatographed on a silica gel, eluent: dichloromethane/methanol 100+3 (v/v).

Concentration of the pure fractions gives 4 g of the expected alcohol.

m.p. = 121° C.

By carrying out the procedure as indicated above, the 2-aminothiazoles described in Table 2 below are prepared.

TABLE 2

[Structure: T—(CH$_2$)$_m$ attached to C=C with S-C(NH$_2$)=N thiazole ring, and phenyl with r$_4$ and r'$_4$ substituents]

| T | r$_4$ | r'$_4$ | m | m.p; °C. |
|---|---|---|---|---|
| —CO$_2$CH$_3$ | H | H | 1 | 231 |
| —OH | H | H | 2 | 121 |
| —COO—CH$_2$CH$_3$ | H | H | 0 | 175 |
| —COO—CH$_2$CH$_3$ | H | H | 1 | 162 |

TABLE 2-continued

| —COO—CH$_2$CH$_3$ | 2-OCH$_3$ | 4-OCH$_3$ | 1 | 117–118 |

PREPARATION C

2-Aminothiazoles substituted in position 5 by a group $$-(CH_2)_m-O-\underset{\underset{O}{\|}}{C}-X_1 \text{ or } -(CH_2)_m-S-X_1$$

2-Amino-5-(1-adamantyl-1-carbonyloxyethyl)-4-phenylthiazole (II: R$_1$ = H; R$_{IV}$ = C$_6$H$_5$;

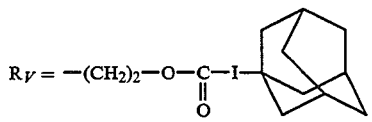

A. 4-(1-Adamantylcarbonyloxy)-1-phenyl-1-butane.

The caesium salt of 1-adamantylcarboxylic acid is prepared according to J. Org. Chem., 1977, 42, 8, 1286, from 12 g of 1-adamantylcarboxylic acid and 10.96 g of caesium carbonate. The salt obtained is dissolved in 70 ml of DMF and then 18 g of 4-iodo-1-phenylbutan-1-one are added and the reaction mixture is refluxed overnight. The DMF is evaporated under vacuum, and the residue resuspended in a 5% solution of Na$_2$CO$_3$ and extracted with CH$_2$Cl$_2$. The organic phase is washed with water and then dried over Na$_2$SO$_4$. It is concentrated under vacuum and the residue is chromatographed on a silica gel, eluent: CH$_2$Cl$_2$.

Concentration of the pure fractions gives 10 g of the expected compound.

B. 2-Amino-5-(1-adamantyl-1-carbonyloxyethyl)-4-phenylthiazole.

10 g of the compound prepared above are dissolved in 100 ml of CC1$_4$ 4.9 g of bromine dissolved in 50 ml of CCl$_4$ are added and the reaction mixture is left stirring for 30 minutes. It is washed with water, and the organic phase decanted, dried over MgSO$_4$, filtered and concentrated under vacuum. The residue is taken up in 50 ml of 95° ethanol. 3.9 g of thiourea are added to the solution and the reaction mixture is left overnight at room temperature. The mixture is concentrated under vacuum, and the residue is taken up in CH$_2$Cl$_2$, washed with a 5% solution of NaHCO$_3$, and the organic phase is decanted, dried over MgSO$_4$, filtered and concentrated under vacuum. The residue is taken up in ether and dried.

m=6.8g; m.p.=167° C.

By carrying out the procedure as indicated above, the 2-aminothiazoles described in Table 3 below are prepared.

TABLE 3

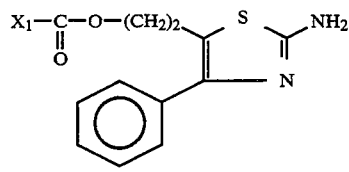

| X$_1$ | m.p; °C. |
|---|---|
| CH$_3$—C(CH$_3$)(CH$_3$)— | 109–110 |
| 2,6-(CH$_3$)$_2$-C$_6$H$_3$— | 129–130 |
| 2,3-(OCH$_3$)$_2$-C$_6$H$_3$— | 147–149 |
| 4-CH$_3$-C$_6$H$_4$— | 190–192 |
| C$_6$H$_5$—S— | 107–108 |

PREPARATION D

Aminothiazoles substituted in position 5 by a group —(CH$_2$)$_m$X in which X represents a group —NX$_1$X$_2$ with X$_1$=X$_2$=H Preparation of 2-amino-5-aminoethyl-4-phenylthiazole.

(II): R$_1$=H; R$_{IV}$=C$_6$H$_5$; R$_V$=—CH$_2$CH$_2$NH$_2$

A) 4-Phthalimido-1-phenylbutan-1-one.

27.4 g of 4-iodo-1-phenylbutan-1-one and 27 g of potassium phthalimide are heated in 100 ml of DMF at 120° C. for 24 hours. The DMF is concentrated under vacuum and the residue is successively washed with water and with a 1N solution of NaOH and extracted with ethyl acetate. The organic phases are decanted, dried over MgSO$_4$, filtered and concentrated under vacuum.

m=11 g.

B) 2-Amino-5-phthalimidoethyl-4-phenylthiazole.

9.6 g of the compound prepared above are dissolved in 50 ml of CCl$_4$ and 80 ml of CH$_2$Cl$_2$. A solution 5.6 g of bromine in 30 ml of CCl$_4$ is added dropwise to the solution. The reaction mixture is washed with water, and the organic phases are dried over MgSO$_4$, filtered and concentrated under vacuum. The residue is taken up 70 ml of ethanol, and 4.5 g of thiourea are added and the reaction mixture is left overnight at room temperature.

The mixture is cooled, and the hydrobromide is separated by filtration, washed with ethanol and then stirred vigorously in a 5% $Na_2CO_3$/ethyl ether mixture. The crystals are filtered.

m=8 g. F=208° C.

C) 2-Amino-5-aminoethyl-4-phenylthiazole.

8 g of the product prepared above are treated with 1.5 g of hydrazine hydrate dissolved in 100 ml of absolute ethanol. The reaction mixture is refluxed overnight and then the following operations are carried out successively: the ethanol is concentrated under vacuum, the residue is taken up in water, acidified by the addition of concentrated HCl up to pH=1, the phtalazinedione separated by filtration, the aqueous phase, cooled on an ice bath, is alkalinised by the addition of concentrated NaOH up to pH=9, the precipitate is filtered, washed with water and dried in an oven.

m=3.7g; m.p.=136°-137° C.

PREPARATION E

2-Aminothiazoles substituted in position 5 by a group $-(CH_2)_mX$ in which X represents a group $-NX_1X_2$ in which $X_1$=H and $X_2$=$-CO-CH_3$ 2-Amino-5-(2-acetylamino-1-ethyl)-4-phenylthiazole.

(II): $R_1$=H; $R_{IV}$=$-C_6H_5$; $R_V$=$CH_3CONH(CH_2)_2-$ 1 g of the 2-aminothiazole obtained according to Preparation D, dissolved in 60 ml of THF, in the presence of 0.7 ml of triethylamine, is treated with 0.44 ml of acetic anhydride dissolved in 20 ml of THF. The reaction mixture is left at room temperature for 2 hours and concentrated under vacuum. The residue is washed with a 5% solution of $NaHCO_3$, and the precipitate is separated by filtration, washed with water and dried.

m=1.12 g; m.p.=208°-209° C.

Using the 2-aminothiazole obtained according to Preparation D, and by carrying out the procedure according to Preparation E, the intermediate compounds described in Table 4 below are prepared.

TABLE 4

T—(CH₂)₂—C(S)(NH₂)=N attached to phenyl ring

| T | m.p; °C. |
|---|---|
| $CH_3-O-C(=O)-NH-$ | 157-158 |
| $CH_3-C(CH_3)(CH_3)-O-C(=O)-NH-$ | oil |
| $CH_3-CH_2-NH-C(=O)-NH-$ | 171 |
| $CH_3-CH_2-NH-C(=S)-NH-$ | 151 |

PREPARATION F

2-Amino-4,5-dihydro-[5,4-d]-thiazolo-[1]-benzoxepin (II): [structure shown]

A) 4-Bromo-4-2H-3,4-dihydro-[1]-benzoxepin-5-one is prepared according to G. Fontaine, P. Maitte, C. R. Acad. Sci., 1964, 258, 4583.

B) 2-Amino-4,5-dihydro-[5,4-d]-thiazolo-[1]benzoxepin.

2.05 g of thiourea are added to 0,027 mole of brominated derivative solubilised in 100 ml of ethanol. The mixture is refluxed for 3 hours. The ethanol is evaporated, the residue is taken up in an aqueous solution of sodium carbonate. It is extracted with ethyl acetate, and the organic phase is dried over $Na_2SO_4$ and evaporated to dryness. 2.4 g of white crystals are obtained.

m.p.=216° C.

PREPARATION G

2-Aminothiazoles substituted in position 5 by a group $-(CH_2)_m-X$ in which m=0 and X represents a $(C_1-C_5)$ alkoxy group or a halogen

Reaction scheme

Stage 1:

$COCH_2Br$ on phenyl with $r_4$ → $COCHO$ on phenyl with $r_4$, via $HO-N(C_2H_5)(C_2H_5)$ according to J. Org. Chem., 1977, 42(4), 754.

Stage 2:

$COCHO$ on phenyl with $r_4$ → $CO-CH(OCH_3)(OCH_3)$ on phenyl with $r_4$, via $Cl-Si-(CH_3)_3$ / $CH_3OH$ according to Synthesis, 1983, 203.

Stage 3:

$CO-CH(OCH_3)(OCH_3)$ on phenyl with $r_4$ → $CO-CH(Br)(OCH_3)$ on phenyl with $r_4$, via $CH_3COBr$ according to J. Chem. Soc., Perkin I, 1981, 2435.

2-Amino-5-methoxy-4-phenylthiazole.

(II): $R_1$=H; $R_{IV}$=$-C_6H_5$; $R_V$=$-OCH_3$ 15.65 g of 2-bromo-2-methoxy-1-phenylethanone and 5.52 g of thiourea are dissolved in 70 ml of methanol. The reaction mixture is refluxed overnight and then concentrated under vacuum. The residue is taken up in a 10% solution of Na$_2$CO$_3$ in water, the mixture is extracted with CH$_2$Cl$_2$, the organic phase is separated and successively dried over Na$_2$SO$_4$, filtered and concentrated under vacuum. The residue is recrystallised from isopropyl ether.

m=7.5g; m.p.=96° C.

TABLE 5

| r$_4$ | m.p; °C. |
|---|---|
| 2-Cl | 72 |
| 2-OCH$_3$ | 159-160 |
| 4-CH$_3$ | 112-114 |

PREPARATION H

Preparation of the indolecarboxylic acids

A) 1-tert-butyloxycarbonylmethylindole-2-carboxylic acid.

a) Benzyl indole-2-carboxylate.

5 g of N,N′-carbonyldiimidazole are introduced into a solution of 5 g of indole-2-carboxylic acid in 50 ml of dry tetrahydrofuran; after stirring for 12 hours at room temperature, 3.7 g of benzyl alcohol are added and the reaction mixture is heated at its reflux temperature; the latter is maintained for 8 hours before removing the solvent by distillation under reduced pressure. The residue is dissolved in ethyl acetate and the organic phase is washed with a 1N aqueous solution of NaOH and then dried before evaporation of the solvent.

The yellow residue is recrystallised from isopropanol.

m.p.=136° C.; yield=85%.

b) Benzyl 1-tert-butoxycarbonylmethylindole-2carboxylate.

80% sodium hydride in oil is added in portions (0.075 mole; 2.25 g) to a solution of benzyl indole-2-carboxylate (0.072 mole; 18.18 g) in 200 ml of dimethylformamide, under a nitrogen atmosphere, at a temperature of between 0° C. and 5° C. The mixture is allowed to reequilibrate to room temperature and the mixture is stirred for 1 hour. tert-Butyl bromoacetate (0.072 mole; 14 g) is then added dropwise at 10° C. The reaction mixture is left for 3 hours at room temperature. The dimethylformamide is evaporated and the residue is successively taken up in water, extracted with methylene chloride, and the organic phase dried over sodium sulphate and evaporated to dryness. 23.8 g of white crystals are obtained by crystallisation of the residue from diisopropyl ether.

m.p.=95° C.

c) 1-tert-Butoxycarbonylmethylindole-2-carboxylic acid.

The ester prepared above (0.065 mole; 23.8 g) is solubilised in a mixture of 400 ml of ethanol and 100 ml of dimethylformamide. 1 g of 5% palladium on carbon is added and the mixture is hydrogenated under atmospheric pressure at room temperature. After stirring for 30 minutes, the theoretical volume of hydrogen is absorbed. The catalyst is filtered on talc and the solvents are evaporated to dryness. A crystallised residue is obtained, which is washed with diisopropyl ether. 15.3 g of white crystals are obtained.

m.p.=177° C.

B) 1-Acetylindole-2-carboxylic acid.

A mixture of indole-2-carboxylic acid (0.06 mole; 10 g), triethylamine (0.15 mole; 21.25 g), acetic anhydride (0.075 mole; 7.5 g) and 4-dimethylaminopyridine (0.006 mole; 0.8 g), in methylene chloride is stirred at room temperature for 18 hours. The reaction mixture is then poured into an aqueous solution of buffer pH=2. The precipitate formed is filtered and then dried in an oven under vacuum. The methylene chloride phase is decanted, dried over sodium sulphate and evaporated to ¾. A second crop of 1-acetylindole-2-carboxylic acid precipitates. The two crops are combined to give 9.4 g of beige crystals.

m.p.=168° C.

C) 1-Benzyloxycarbonylaminoindole-2-carboxylic acid.

8 g of indole-2-carboxylic acid are dissolved in 120 ml of dichloromethane and then 10 g of triethylamine and 1 g of 4-dimethylaminopyridine are added.

The reaction mixture is stirred and then cooled to 0°-5° C. 8.5 g of benzyloxycarbonyl chloride are added dropwise at a temperature of less than 5° C. The mixture is left stirring overnight and then concentrated under vacuum. The residue is taken up in 500 ml of ethyl acetate and then filtered. The mother liquors are concentrated under vacuum and taken up in 50 ml of dichloromethane. The mother liquors are filtered and concentrated under vacuum.

m=2.4 g of oil; NMR (DMSO): 2 H at 5.38 (s, CH$_2$—C$_6$H$_5$); 10 H between 7.0 and 8.0 (m; Har).

D) 1-tert Butyloxycarbonylindole-2-carboxylic acid 30 ml of a solution of 6 g of di-tert-butyl dicarbonate are introduced dropwise into 30 ml of a solution of 4 g of indole-2-carboxylic acid, 4 ml of triethylamine and 0.4 g of 4-dimethylaminopyridine in acetonitrile. After stirring for 2 hours at room temperature and removing the precipitate formed, the acetonitrile is removed by distillation and the reside is dissolved in methylene chloride. The organic phase is washed with water, dried and concentrated to dryness.

m.p.=117° C.; yield 66%; yield=66%.

EXAMPLE 1

2-[(2-Indolyl)carbonylamino]-4-(2,4-dimethoxyphenyl)-5-benzylthiazole (I): R$_1$ = H; Z =

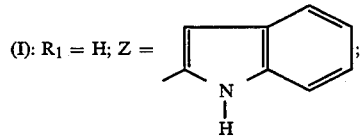

R$_{IV}$ =

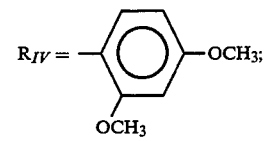

R$_V$ = —CH$_2$—C$_6$H$_5$ 1.96 g of 2-amino-4-(2,4-dimethoxyphenyl)-5-benzyl-thiazole prepared above according to Preparation A, 1.22 g of 1-acetylindole-2-carboxylic acid, 0.85 g of triethylamine and 2.95 g of BOP are dissolved in 20 ml of dimethylformamide.

The reaction mixture is stirred for 24 hours at room temperature and then poured into a buffer solution, pH=2. A yellow precipitate is separated by filtration, washed with water and dissolved in ethyl acetate. The solution is washed successively with a buffer solution, pH=2, with water, with a 5% solution of $NaHCO_3$ and with water, and then dried over $MgSO_4$ and concentrated under vacuum. The residue is purified by chromatography on a silica gel, eluent: dichloromethane/ethyl acetate 98/2 (v/v).

Concentration of the pure product fractions gives a residue which is treated, with stirring for 24 hours, with 3 g of $Na_2CO_3$ in 80 ml of methanol. The methanol is concentrated under vacuum and the residue is taken up in a water/ether mixture. A white precipitate is separated by filtration and washed with ether.

m=0.97 g; m.p.=201°-202° C.

The compounds according to the invention, which are described in Table 6 below, are prepared in the same manner.

TABLE 6

| Example n° | $R_V$ | m.p; °C. |
|---|---|---|
| 2 | —CH₂—(cyclohexyl) | 225 |
| 3 | phenyl | 272 |
| 4 | 2-methoxyphenyl | 262 |
| 5 | 3-methoxyphenyl | 225 |
| 6 | 4-methoxyphenyl | 283 |

EXAMPLE 7

2-[(1-tert-Butoxycarbonyloxymethyl-2-indolyl)carbonylamino ]-4-phenyl-5-hydroxyethylthiazole.

(I): $R_V=$ —(CH₂)₂—OH; $R_{IV}=$ —C₆H₅; $R_1=$ H;

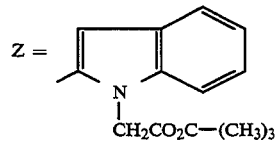

2 g of the aminoalcohol prepared above (according to Preparation B, Table 2), 2.75 g of 1-tert-butoxycarbonylindole-2-carboxylic acid, 1.4 g of triethylamine and 4.9 g of BOP are dissolved in 15 ml of dimethylformamide. After leaving overnight at room temperature, the reaction mixture is poured into phosphate buffer, pH=2. A precipitate is separated by filtration, washed with water and dissolved in ethyl acetate. The solution is successively washed with a 5% solution of $NaHCO_3$ and with water, separated by decantation, and the organic phase is dried over $MgSO_4$ and concentrated under vacuum.

The residue is purified by chromatography on a silica gel, eluent : dichloromethane/methanol 100+0.5 (v/v).

The first product eluted corresponds to the deacylated compound (O and N acylation, m.p.=70° C.).

The expected product is the second to be eluted.

m=1.2 g; m.p.=180°-181° C.

EXAMPLE 8

2-[(1-tert-Butoxycarbonylmethyl-2-indolyl)carbonylamino]-4-phenyl-5-acetoxyethylthiazole

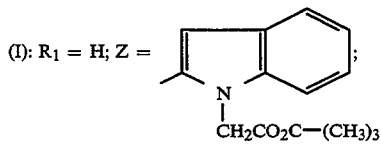

$R_{IV}=$ —C₆H₅; $R_V=$ CH₃—COO—(CH₂)₂—

0.30 g of the product prepared above is suspended in 5 ml of pyridine.

1.2 ml of acetic anhydride are added and the reaction mixture is stirred overnight at room temperature. The mixture is then poured into sulphate buffer, pH=2, and a precipitate is separated by filtration, washed with water and then taken up in dichloromethane. The solution is successively washed with a 5% solution of $NaHCO_3$, separated by decantation, and the organic phase is dried over $MgSO_4$, filtered and concentrated under vacuum. The residue is purified by chromatography on a silica gel, eluent: dichloromethane/ethyl acetate 98/2 (v/v).

m=0.16g; NMR (DMSO): 9 H at 1.48 (S, t-BuO₂C); 3 H at 2.00 (S, CH₃CO₂); 2 H at 3.24 ( T, J=7 Hz, CH₂ thiazole); 2 H at 4.30 (T, J=7 Hz, CH₂OAc); 2 H at 5.40 ( S, CH₂CO₂t-Bu ); 10 H between 7.2 and 7.9 (M, Bar); 1 H at 12.8 (S, NHCO).

EXAMPLE 9

2-[(1-Carboxylmethyl-2-indolyl)carbonylamino]-4-phenyl-5-acetoxyethylthiazole

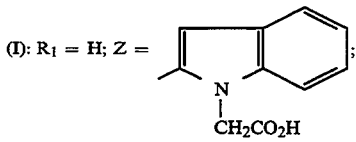

(I): $R_1$ = H; Z =

$R_{IV}$ = $C_6H_5$; $R_V$ = $CH_3$—COO—$(CH_2)_2$—

0.15 g of the compound prepared above is solubilised in 2 ml of anisole and 10 ml of trifluoroacetic acid.

The mixture is left for 45 minutes at room temperature and then concentrated under vacuum. The residue obtained is washed with a mixture of hexane and diethyl ether (50/50) and then dried.

m=0.14g; m.p.=217°-218° C.

EXAMPLE 10

2-[(1-Acetyl-2-indolyl)carbonylamino]-4-(2,4-dimethoxyphenyl)-5-ethoxycarbonylmethylthiazole

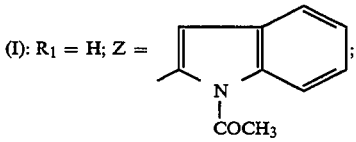

(I): $R_1$ = H; Z =

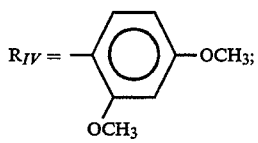

$R_{IV}$ =

$R_V$ = $CH_3CH_2$—OCO—$CH_2$—

1.5 g of 2-amino-4-(2,4-dimethoxyphenyl)-5-ethoxycarbonylmethylthiazole, 1 g of 1-acetylindole-2carboxylic acid, 0.7 ml of triethylamine and 2.39 g of BOP are dissolved in 15 ml of dichloromethane. The reaction mixture is stirred overnight at room temperature and then concentrated under vacuum. The residue is taken up in ethyl acetate and the solution is successively washed with a buffer solution, pH=2, with a 5% solution of NaHCO$_3$ and with water, and then the organic phase is dried over MgSO$_4$ and concentrated under vacuum. The residue is purified by chromatography on a silica gel, eluent: dichloromethane/ethyl acetate 100/2.5 (v/v).

m=1.2 g; m.p.=130°-135° C.

EXAMPLE 11

2-[(2-Indolyl)carbonylamino]-5-ethoxycarbonyl-4-phenylthiazole

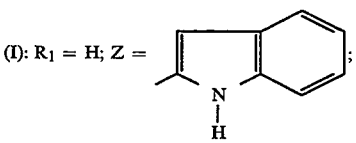

(I): $R_1$ = H; Z =

-continued $R_{IV}$ = —$C_6H_5$; $R_V$ = $CH_3CH_2$—OCO—

By carrying out the procedure according to Example 10 which is described above, the compound 2-[(1-acetyl-2-indolyl ) carbonylamino]-4-phenyl-5-ethoxycarbonylthiazole (1.5 g) is prepared and dissolved in 100 ml of ethanol in the presence of 0.6 g of Na$_2$CO$_3$. The mixture is stirred at room temperature for 48 hours and then concentrated under vacuum. The residue is triturated in water and then in a minimum amount of dichloromethane, filtered and dried.

m=1.1 g; m.p.=248° C.

EXAMPLE 12

2-[(2-Indolyl)carbonylamino]-4-(2,4-dimethoxyphenyl)-5-carboxymethylthiazole

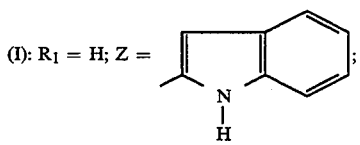

(I): $R_1$ = H; Z =

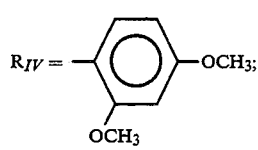

$R_{IV}$ =

$R_V$ = —$CH_2$—COOH 0.5 g of 2-[(1-acetyl-2-indolyl)carbonylamino]-4-(2,4-dimethoxyphenyl)-5-ethoxycarbonylmethylthiazole, prepared above according to Example 10, is dissolved in 10 ml of 95° ethanol and then 1.5 ml of 2N NaOH are added. The reaction mixture is stirred,overnight at room temperature and then concentrated under vacuum. The residue is taken up in a buffer solution, pH=2, a precipitate is separated by filtration, washed with water, filtered and then rinsed with ether.

m=0.28g; m.p.=284° C.

By carrying out the procedure according to Examples 7 to 12 above, the compounds described in Table 7 below are prepared.

TABLE 7

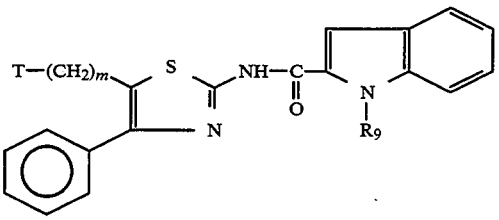

| Example No. | T | m | $R_9$ | m.p.; °C. |
|---|---|---|---|---|
| 13 | —CO$_2$CH$_3$ | 1 | H | 254 |
| 14 | —CO$_2$CH$_3$ | 2 | H | 181 |
| 15 | —OH | 2 | —CH$_2$CO$_2$H | 131 |
| 16 | —OH | 2 | H | 242 |
| 17 | —OH | 3 | H | 213 |
| 18 | —OCOCH$_3$ | 2 | H | 168 |
| 19 | —OCOCH$_3$ | 3 | H | 192 |
| 20 | —O—CO—C$_6$H$_5$ | 2 | —CH$_2$CO$_2$H | 216 |
| 21 | —O—CO-tert-Bu | 2 | H | 229 |
| 22 | —CO$_2$H | 1 | H | 266 |
| 23 | —CO$_2$H | 2 | H | >300 |

TABLE 7-continued

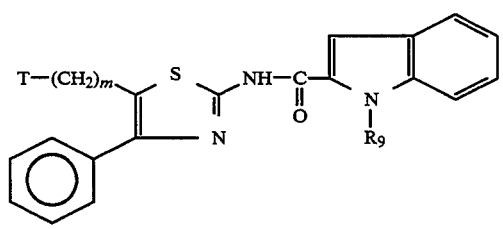

| Example No. | T | m | $R_9$ | m.p.; °C. |
|---|---|---|---|---|
| 24 | —$CO_2H$ | 2 | —$CH_2$—$CO_2H$ | 239–240 |
| 25 | —$CO_2H$ | 1 | —$CH_2$—$CO_2H$ | 199–200 |
| 26 | —$CO_2CH_3$ | 2 | —$CH_2$—$CO_2H$ | 202–203 |
| 27 | —$CO_2CH_3$ | 1 | —$CH_2$—$CO_2H$ | 183–185 |
| 28 | —C(=O)—N—$(CH_3)_2$ | 1 | —$CH_2$—$CO_2H$ | 252 |
| 29 | —C(=O)—N(H)—$CH_3$ | 1 | —$CH_2$—$CO_2H$ | 233–234 |
| 30 | —C(=O)—N(pyrrolidinyl) | 1 | —$CH_2$—$CO_2H$ | 241–242 |

EXAMPLE 31

2-[(2-Indolyl)carbonylamino]-4-phenyl-5-[2-(1-pyrrolidinocarbonyl)-1-ethyl]thiazole

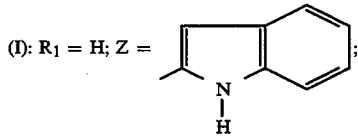

(I): $R_1$ = H; Z =

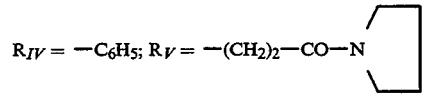

$R_{IV}$ = —$C_6H_5$; $R_V$ = —$(CH_2)_2$—CO—N(pyrrolidinyl)

0.5 g of the ester described in Example 14 is added to 5 ml of pyrrolidine, the mixture is stirred overnight at room temperature and then poured into a buffer solution, pH=2. A precipitate is separated by filtration and then dissolved in ethyl acetate. The solution is washed with a buffer solution, pH=2, and then with water, and the organic phase is separated by decantation, dried over $MgSO_4$ and concentrated under vacuum.

m=0.48g; m.p.=179° C.

By carrying out the procedure according to Example 10 above, compounds 32 to 51, which are described in Table 8 below, are prepared.

TABLE 8

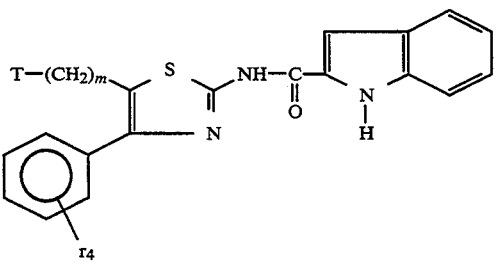

| Example No. | T | m | $r_4$ | m.p.; °C. |
|---|---|---|---|---|
| 32 | —$COOCH_3$ | 1 | 4-F | 224–225 |
| 33 | —$COOC_2H_5$ | 1 | 2-Cl | 178 |
| 34 | —N($C_2H_5$)$_2$ | 1 | H | 180 |
| 35 | —C(=O)—N(pyrrolidinyl) | 1 | H | 239 |
| 36 | —C(=O)—N(pyrrolidinyl) | 1 | 4-F | 243–244 |
| 37 | —C(=O)—N(pyrrolidinyl) | 1 | 2-Cl | 187–188 |
| 38 | —$NH_2$ | 2 | H | 202–203 |
| 39 | —NH—C(=O)—$CH_3$ | 2 | H | 261–262 |
| 40 | —O—C(=O)—$CH_3$ | 2 | 4-F | 188–189 |
| 41 | —O—C(=O)—$OCH_3$ | 2 | H | 208–209 |
| 42 | —NH—C(=O)—O-tert-Bu | 2 | H | 223–224 |
| 43 | —NH—C(=O)—O—$CH_3$ | 2 | H | 264 |
| 44 | —NH—C(=O)—N(H)—$C_2H_5$ | 2 | H | 248–249 |
| 45 | —NH—C(=O)—$(CH_2)_2$—$CO_2H$ | 2 | H | 275–276 |
| 46 | —NH—C(=S)—N(H)—$C_2H_5$ | 2 | H | 209–210 |

TABLE 8-continued

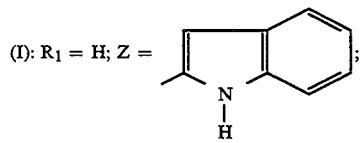

| Example No. | T | m | r4 | m.p.; °C. |
|---|---|---|---|---|
| 47 | 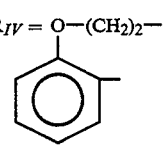 | 2 | H | 196-197 |
| 48 | —O—C(=O)—(2,6-(OCH₃)₂C₆H₃) | 2 | H | 218-219 |
| 49 | —O—C(=O)—(2,6-(CH₃)₂C₆H₃) | 2 | H | 140-142 |
| 50 | —O—C(=O)—C₆H₄—CH₃ | 2 | H | 270-271 |
| 51 | —S—C₆H₅ | 2 | H | 212-213 |

EXAMPLE 52

2-[(2-Indolyl)carbonylamino]-4-phenyl-5-phenylaminocarbonyloxyethylthiazole

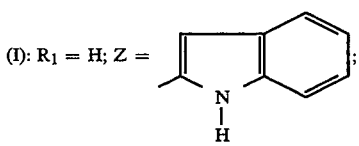

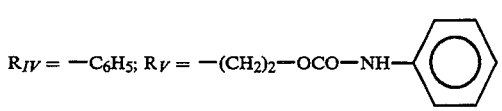

$R_{IV}$ = —C₆H₅; $R_V$ = —(CH₂)₂—OCO—NH—C₆H₅

A) 2-[(1-Acetyl-2-indolyl)]carbonylamino-4-phenyl-5-phenylaminocarbonyloxyethylthiazole.

0.7 g of the alcohol prepared according to Example 16 and 0.2 ml of phenyl isocyanate are stirred overnight at room temperature in 5 ml of dichloromethane. The precipitate formed is separated by filtration and then purified by chromatography on a silica gel, eluent: dichloromethane/ethyl acetate 95/5 (v/v).

m=0.52 g; m.p.=156° C.

B) Compound 52

0.5 g of the compound prepared above is dissolved in 30 ml of ethanol and 5 ml of water and then 0.21 g of Na₂CO₃ is added.

The reaction mixture is stirred overnight at room temperature and then concentrated under vacuum. The residue is taken up in ethyl acetate and washed successively with a solution of Na₂CO₃ and with water. The organic phase is separated by decantation and concentrated under vacuum. The residue is taken up in ether.

m=0.4 g; m.p.=249° C.

EXAMPLE 53

2[(2-Indolyl)carbonylamino]-4,5-dihydro-[5,4-d]-1H-thiazolobenzoxepin (I): $R_1$ = H; Z =

$R_V$ and $R_{IV}$ = O—(CH₂)₂—C₆H₄

1 g of the thiazole prepared above (Preparation F), 2.6 g of BOP, 0.93 g of 1-acetylindole-2-carboxylic acid and 0.46 g of triethylamine are mixed in 30 ml of dimethylformamide. The reaction mixture is stirred for 30 hours at room temperature. The dimethylformamide is evaporated, and the residue is taken up in ethyl acetate and washed with water. The organic phase is dried over sodium sulphate and evaporated. The residue is chromatographed on a silica gel, eluent: dichloromethane/methanol 100+0.5 (v/v). 0.9 g of a yellow foam is obtained and it is solubilised in dichloromethane to which ethanol (100 ml) has been added. 10 ml of 2N NaOH are added and the mixture is stirred at room temperature for 1 hour. After evaporation of the organic solvents, the residue is taken up in ethyl acetate and washed with a buffer solution, pH=2. The organic phase is dried over MgSO₄, filtered and evaporated. Yellow crystals are obtained which are then washed with dichloromethane and then with ethanol.

m=0.45 g; m.p. >260° C.

EXAMPLE 54

2-[(2-Indolyl)carbonylamino]-4-phenyl-5-(1-piperidinyl)thiazole

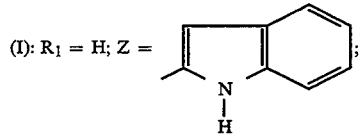

$R_{IV} = $ —C$_6$H$_5$; $R_V = $ 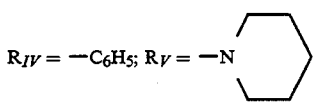

A) 2-Amino-4-phenyl-5-(1-piperidinyl)thiazole.

A mixture of 1 g of 2-amino-4-phenyl-5-bromothiazole and 1.7 g of piperidine in 25 ml of absolute ethanol is refluxed for 48 hours. The ethanol is concentrated under vacuum and the residue is taken up in 50 ml of water and 10 ml of 30% NaOH. It is extracted with ethyl acetate, and the organic phase is dried over Na$_2$CO$_4$ and filtered. The solution is concentrated under vacuum and the residue is recrystallised from isopropyl ether.

m=0.41 g; m.p=135°–137° C.

B) Compound 54

0.4 g of the product obtained above is dissolved in 50 ml of dichloromethane. 0.33 g of 1-acetylindole-2-carboxylic acid, 0.82 g of BOP and 0.19 g of triethylamine are added successively. The reaction mixture is stirred for 4 days at room temperature. 25 ml of water are added and the organic phase is separated by decantation, dried over Na$_2$SO$_4$ and concentrated under vacuum. The residue is taken up in 50 ml of absolute ethanol, and 10 ml of 2.5N NaOH are added and the mixture is stirred for 3 hours at room temperature. The mixture is concentrated under vacuum, and the residue is taken up in 50 ml of water, extracted with ethyl acetate, and the organic phase is separated by decantation, dried over Na$_2$SO$_4$ and concentrated under vacuum. The residue is recrystallised from ethyl acetate.

m=0.26 g; m.p. >260° C.

By carrying out the procedure according to Example 54, the compounds 55 and 56, which are described in Table 9 below, are prepared.

TABLE 9

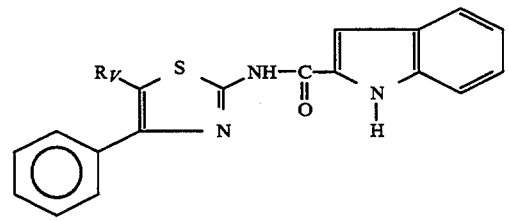

| Example No. | R$_V$ | m.p.; °C. |
|---|---|---|
| 55 | —N⟩—OH (piperidinyl-OH) | >300 |
| 56 | —N⟩N—C(=O)—O—C$_2$H$_5$ | 247–249 |

EXAMPLE 57

2-[(2-Indolyl)carbonylamino]-5-bromo-4-phenylthiazole (I): R$_1$ = H; Z = 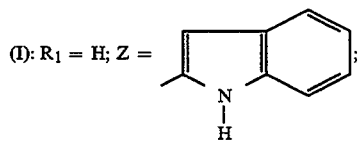

R$_{IV}$ = —C$_6$H$_5$; R$_V$ = Br 3.9 g (0.015 mole) of 2-amino-5-bromothiazole are dissolved in 60 ml of dichloromethane.

3.26 g of 1-acetylindole-2-carboxylic acid, 8.1 g of BOP, 1.85 g of triethylamine are added, and the reaction mixture is stirred at room temperature for 8 days and then 100 ml of an aqueous solution which is buffered to pH=2 are added, and the mixture is decanted, and the organic phase is dried over Na$_2$SO$_4$ and concentrated under vacuum. The residue is taken up in 100 ml of methanol and then 5 g of Na$_2$CO$_3$ are added. The mixture is stirred for three hours at room temperature, concentrated under vacuum at low temperature, and taken up in 100 ml of an aqueous solution which is buffered to pH=2, extracted with ethyl acetate and the organic phase is dried over Na$_2$SO$_4$. The mixture is filtered and concentrated under vacuum. The residue is chromatographed on a silica gel, eluent: CH$_2$Cl$_2$. After removing the top impurities, the expected product is eluted, and it is recrystallised, after evaporation of the solvent, from a CH$_2$Cl$_2$/diisopropyl ether mixture.

m=2.8g; m.p.=224°–226° C.

EXAMPLE 58

2-[(2-Indolyl)carbonylamino]-5-methoxy-4-phenylthiazole (I): R$_1$ = H; Z = 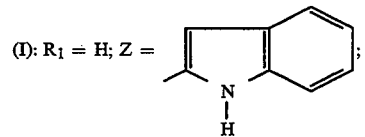

R$_{IV}$ = —C$_6$H$_5$; R$_V$ = —OCH$_3$ 3.15 g of 2-amino-5-methoxy-4-phenylthiazole are dissolved in 60 ml of CH$_2$Cl$_2$. 3.26 g of 1-acetylindole-2-carboxylic acid, 8.12 g of BOP and 1.86 g of triethylamine are added, and the reaction mixture is stirred at room temperature for one week. 50 ml of water are added and the organic phase is decanted, dried over Na$_2$SO$_4$, filtered and concentrated under vacuum. The residue is taken up in 100 ml of methanol, and 10 g of K$_2$CO$_3$ are added and the mixture is stirred overnight at room temperature. The mixture is concentrated under vacuum, and the residue is taken up in water, and the precipitate formed is separated by filtration and washed with CH$_2$Cl$_2$.

m=1.7 g; m.p. >260° C.

By carrying out the procedure according to the example above, the compounds 59 to 61, which are described in Table 10 below, are prepared.

TABLE 10

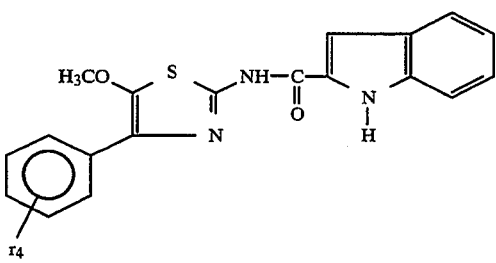

| Example No. | r4 | m.p.; °C. |
|---|---|---|
| 59 | 2-Cl | 260-262 |
| 60 | 4-CH3 | 252-254 |
| 61 | 2-OCH3 | 248-250 |

EXAMPLE 62

2-[(2-Indolyl)carbonylamino]-5-hydroxy-4-phenyl-thiazole

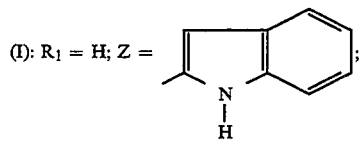

(I): $R_1$ = H; Z =

$R_{IV}$ = —$C_6H_5$; $R_V$ = —OH 0.58 g of the thiazole prepared according to Example 58 are dissolved in 100 ml of $CH_2Cl_2$. 4.98 ml of a 2M solution of boron tribromide in $CH_2Cl_2$ are added at room temperature and the reaction mixture is left stirring for 24 hours. 4.98 ml of $BBr_3$ are again added, the mixture left for 5 days at room temperature and 4.98 g of $BBr_3$ are finally added and the reaction mixture is left at room temperature for 48 hours. It is then adjusted to pH=5-6 by the addition of a 4N solution of NaOH and then the organic phase is extracted with 2 times 50 ml of 4N NaOH. The aqueous phase is neutralised by adding a 2N solution of HCl. The mixture is extracted with $CH_2Cl_2$, and the organic phases are dried over $Na_2SO_4$, filtered and concentrated under vacuum to produce a residue which crystallises.

m=0.5g; m.p.=237°-239° C.

We claim:

1. A 2-acylaminothiazole of formula:

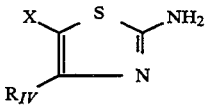

in which $R_{IV}$ is selected from the group consisting of ($C_3$-$C_7$) cycloalkyl, ($C_1$-$C_4$)alkyl substituted ($C_3$-$C_7$)cycloalkyl, phenyl and phenyl substituted by one or more groups selected from halogen, ($C_1$-$C_6$) alkyl, ($C_1$-$C_3$)alkoxy, ($C_1$-$C_3$)thioalkoxy, nitro and trifluoromethyl, and X is selected from the group consisting of ($C_1$-$C_5$)alkoxy, piperidinyl, 4-hydroxy piperidinyl and 4-($C_1$-$C_3$)-alkoxycarbonyl piperazinyl.

2. A compound of formula:

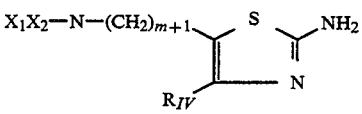

in which $R_{IV}$ is selected from the group consisting of ($C_3$-$C_7$-)cycloalkyl, ($C_1$-$C_4$)alkyl substituted ($C_3$-$C_7$)cycloalkyl, phenyl and phenyl substituted by one or more groups selected from halogen, (Cl-$C_6$) alkyl, ($C_1$-$C_3$) alkoxy, ($C_1$-$C_3$)thioalkoxy, nitro and trifluoromethyl, m is selected from 1 and 2, and —$NX_1X_2$ is selected from the group consisting of phtalimido and —$NH_2$, or a salt thereof.

* * * * *